US010362990B2

(12) United States Patent
Warner et al.

(10) Patent No.: US 10,362,990 B2
(45) Date of Patent: Jul. 30, 2019

(54) PASSIVE CATHETER IDENTIFICATION AND SELF-CONFIGURATION SYSTEM

(71) Applicant: General Electric Company, Schenectady, NY (US)

(72) Inventors: Adrian F. Warner, Wauwatosa, WI (US); Claudio P. Mejia, Wauwatosa, WI (US); Daniel R. Schneidewend, Wauwatosa, WI (US); Rodger F. Schmit, Wauwatosa, WI (US); Nicholas P. Nekich, Wauwatosa, WI (US); Timothy P. Stiemke, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 908 days.

(21) Appl. No.: 14/582,272

(22) Filed: Dec. 24, 2014

(65) Prior Publication Data

US 2016/0184025 A1   Jun. 30, 2016

(51) Int. Cl.

| | |
|---|---|
| *A61B 5/04* | (2006.01) |
| *A61B 5/00* | (2006.01) |
| *A61B 5/042* | (2006.01) |
| *A61B 90/90* | (2016.01) |
| *A61B 90/92* | (2016.01) |
| *A61B 90/98* | (2016.01) |
| *A61B 5/0432* | (2006.01) |

(52) U.S. Cl.
CPC ............ *A61B 5/6852* (2013.01); *A61B 5/042* (2013.01); *A61B 90/90* (2016.02); *A61B 90/92* (2016.02);

(Continued)

(58) Field of Classification Search
CPC .............. A61B 19/44; A61B 2019/444; A61B 2019/448; A61B 2560/029;
(Continued)

(56) References Cited

U.S. PATENT DOCUMENTS 4,623,976 A * 11/1986 Carp .................... G01R 31/007
702/90
4,856,530 A    8/1989 Vandervelden
(Continued)

FOREIGN PATENT DOCUMENTS

CA      1200852      2/1986

OTHER PUBLICATIONS

"ThermoCool SF NAV Catheter With Curve Visualization" Biosense Webster, Inc., 2012, 2 pages.
(Continued)

*Primary Examiner* — Amanda K Hulbert
(74) *Attorney, Agent, or Firm* — Boyle Fredrickson, S.C.

(57) ABSTRACT

In the present invention, a catheter identification system for providing information about one or more attributes of a catheter connectable to an electrophysiology (EP) recording or mapping system includes a catheter, a resistor network operably connected to the catheter, the resistor network including at least one identification resistor and an identification resistor measurement circuit operably connected to the catheter and configured to send an identification signal through the at least one resistor in the resistor network to retrieve an altered identification signal from the identification resistor, where the altered identification signal provides information on an attribute of the catheter.

14 Claims, 2 Drawing Sheets

(52) U.S. Cl.
CPC ............ *A61B 90/98* (2016.02); *A61B 5/0432* (2013.01); *A61B 2560/029* (2013.01); *A61B 2562/226* (2013.01)

(58) Field of Classification Search
CPC . A61B 2562/226; A61B 5/042; A61B 5/0432; A61B 5/6852
See application file for complete search history.

(56) References Cited

U.S. PATENT DOCUMENTS

| | | | |
|---|---|---|---|
| 5,720,293 A * | 2/1998 | Quinn | A61B 5/028 600/505 |
| 6,623,423 B2 * | 9/2003 | Sakurai | A61B 17/320068 600/104 |
| 8,435,232 B2 | 5/2013 | Aeby et al. | |
| 2008/0255504 A1 | 10/2008 | Nekich et al. | |

OTHER PUBLICATIONS

"Ablate With ThermoCool Catheters, Far-Reaching Effects", Biosense Webster, Inc., 2009, 4 pages.
"Smooth Torque Control. Superb Handling", Biosense Webster, Inc., May 29, 2012, 2 pages.
"Shaped Far The HIS. Designed for Stability.", Biosense Weloseter, Inc., 2012, 2 pages.
"Reengineered for a Greener Future", LassoNav eco Catheter, Biosense Webster, Inc., undated, 5 pages.

* cited by examiner

PASSIVE CATHETER IDENTIFICATION AND SELF-CONFIGURATION SYSTEM

BACKGROUND OF INVENTION

The invention relates generally to catheters, and more particularly to catheters including identification systems that enable the catheters to be specifically identified by the electrophysiological (EP) and other recording or mapping device or system to which the catheters are connected during studies or monitoring of patients.

Catheters are used in an increasing number of medical procedures to evaluate various conditions of the patient with which the catheter is utilized. As a result, there are many different configurations of catheters that are constructed for use in the procedures.

While many different configurations of catheters can be utilized for a particular procedure, the exact configuration of the catheter in use must be identified to or by the recording or mapping device to which the catheter is connected in order for the device to correctly receive or transmit signals in the procedure using the selected catheter.

To identify the particular catheter and its configuration to the associated recording or mapping device, prior art catheters have employed electrically alterable erasable programmable read-only memory (EPROM) chips or other suitable electronic storage devices directly within the construction of the catheter to contain an identity tag associated with the particular catheter and it configuration. On connection to a compatible recording or mapping system, the memory chip can be accessed by the device to provide various information stored about the individual catheter, such as the catheter type and manufacturer, as well as the total time the catheter has been in use, as recorded in the memory chip. Using the information on the chip, the device or system can determine whether the catheter is compatible with the device for the intended procedure, as well as to reject a reused or reprocessed catheter that has exceeded a use threshold.

Other prior art solutions to this problem involving disposable catheters use radio frequency identification (RFID) tagging within the catheter to identify and provide use information on the catheter to the system when connected to the system.

In each of these prior art identification systems, while the EPROM chip and RFID tag provide the desired information about the catheter to the recording or mapping system using the catheter, these system require significant increases in complexity and expense to manufacture the catheters with these devices. Further, the recording and mapping systems with which these catheters are used must also be capable of identifying and receiving the information provided by the EPROM chops and/or RFID tags for the catheters to be recognized. As such, prior art EP recording and mapping system require that the catheter configurations be made physically by the user through a manual interface of the EP system A more simplistic prior art solution for identifying a particular catheter is to provide the particular catheter with a keyed connector having a color code thereon to identify the catheter. However, this solution is difficult to utilize based on wide range of catheters currently in use. Also, this solution again requires that the physician or other individual manually input all of the information provided about the catheter by the color code into the system, requiring a significant amount of additional time and effort.

Accordingly, it is desirable to develop a passive system for the identification of the relevant information about a catheter to a system to which the catheter is connected for use in a medical procedure. The identification system should allow either manual identification of the catheter at the input connection, or automatic configuration on connection of the catheter to the system. When the catheter information can be detected by an associated recording or mapping system, the system can operate using a catheter configuration basis instead of or in addition to a classical study configuration method.

BRIEF DESCRIPTION OF THE INVENTION

There is a need or desire for a system to passively identify a catheter to a recording or mapping system to which the catheter has been connected. The abovementioned drawbacks and needs are addressed by the embodiments described herein in the following description.

According to one exemplary aspect of the invention, a passive catheter identification system includes a catheter having a resistor network disposed within or on the catheter, where the resistor network provides relevant information about the particular catheter based on the resistance values for the individual resistors forming the resistor network. The identification system supports multiple connection identification methods around one core, simple concept involving a robust construction with very few parts that may fail. The resistor network is located within an identification circuit on the catheter that allows signals from the recording or mapping system to be sent through the identification circuit. These signals interact with the individual resistors present in the identification circuit and provide return signals to the system that include information to the recording or mapping system about various attributes of the catheter. The attributes identified by the resistors can include one or more of the type of catheter, the number of poles (configuration), and the manufacturer. Using one resistor value per attribute, the identification circuit for the identification system has a significant range of catheters types, configuration and manufacturers that can be identified. Once the recording system has identified the catheter, type, manufacturer, and device type, this information can be used by the recording system to configure the catheters being used in the procedure.

According to another exemplary aspect of the invention, the resistor network in the identification circuit has the capability to monitor the connection resistance through the identification circuit. In doing so, the passive system provides the recording or mapping system with any variance to the standard specification for the connection, which can alert the system to connectivity issues. The identification system and/or circuit can thus additionally provide a measurement quality calibration channel as a quality check on the connection to highlight poor resistance connections which typically increase noise susceptibility of the system and can be a sign of worn signal path cabling, or other issues with the catheter.

According to still another exemplary aspect of the invention, the identification system can be implemented in a number of physical manners to accommodate new and existing catheter constructions, such as in the catheter, the catheter cable, or in a catheter interface block or input module. In particular, the identification system can be disposed directly in the catheter cable connector when the catheter is manufactured, as the catheter identification system is low-tech, low cost, and easy for device manufacturers to implement. Additionally, the identification system components can be disposed within the adaptor cable used to connect the catheter to the recorder or mapping system catheter interface blocks. Further, the identification system can be positioned within a custom catheter interface adaptor block on the recorder, and to provide interface indicator blocks, such as those disclosed in US Patent Application Publication No. 2008/0255504, which is expressly incorporated herein by reference in its entirety. The catheter blocks include the identification information regarding catheter identification system, such that the connection of the catheter to the catheter input module (CIM) to specified inputs would allow the system to auto-detect the associated catheter identification system to use with the system.

According to a further exemplary aspect of the invention, in addition to the resistor network, a color code indicator can be displayed on the exterior of the catheter to physically identify catheters relative to the identification block. Further, with regard to the resistance values of the individual resistors in the resistor network that provide attribute information on the catheter, this information can be provided in a look-up table, on the recording or mapping system and/or in a physical format, to identify catheter types, manufacturers, and catheter configuration based on the resistor values. The table can be updated to include new device types and manufacturers in an easy and readily available manner.

According to still a further exemplary aspect of the intention, the identification system of the invention also enables automated device configuration by the system such that the system knows what catheter is connected where with respect to the amplifier. This method of catheter identification and configuration leads to the ability to define study configurations based on the catheter connected to the system rather than current methods, i.e. the catheter configuration could be set based on the catheter or device used during the procedure. In addition, the system can not only be physically set up and/or defined by the physician, but the computer software in the system can be adapted to respond to the catheter types connected. In this way user settings for this device(s) type configuration can be automatically loaded from memory to speed-up procedure setup time.

According to still another exemplary aspect of the invention, the catheter identification system greatly simplifies catheter connection and configuration relative to the receiving amplifier, particularly when positioned within a direct catheter connection. The identification system is flexible, and supports legacy 2 mm pin connectors but provides a suitable configuration to enable easier hook-up with improved accuracy and reduced mistakes relative to connection of the physical catheter According to another aspect of the invention, a method of identifying one or more attributes of a catheter connected to an EP system includes the steps of providing a passive catheter identification system operably connected between at least one catheter and a catheter interface forming a part of the EP system, the identification system including an identification resistor measurement circuit engaged with the catheter interface and operable to output an identification signal and an identification resistor network engaged with at least one catheter and operably engageble with the identification resistor measurement circuit, the resistor network including at least one identification resistor capable of receiving the identification signal and outputting an altered identification signal indicative of an attribute of the catheter, connecting the at least one catheter to the catheter interface, outputting an identification signal from the identification resistor measurement circuit to the resistor network, receiving an altered identification signal from the resistor network and determining a catheter attribute corresponding to the altered identification signal.

According to a further aspect of the invention, a catheter identification system for providing information about one or more attributes of a catheter connectable to an electrophysiology (EP) recording or mapping system includes a catheter, a resistor network operably connected to the catheter, the resistor network including at least one identification resistor and an identification resistor measurement circuit operably connected to the catheter and configured to send an identification signal through the at least one resistor in the resistor network to retrieve an altered identification signal from the identification resistor, where the altered identification signal provides information on an attribute of the catheter.

According to still another aspect of the invention, an EP system for obtaining and recording information on a patient connected to the FP system includes an amplifier including a catheter interface, a computer operably connected to the amplifier, at least one catheter connected to the catheter interface and a passive catheter identification system operably connected between the at least one catheter and the catheter interface, the identification system having an identification resistor measurement circuit engaged with the catheter interface and operable to output an identification signal and an identification resistor network engaged with the at least one catheter and operably engageble with the identification resistor measurement circuit, the resistor network including at least one identification resistor capable of receiving the identification signal and outputting an altered identification signal indicative of an attribute of the catheter.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
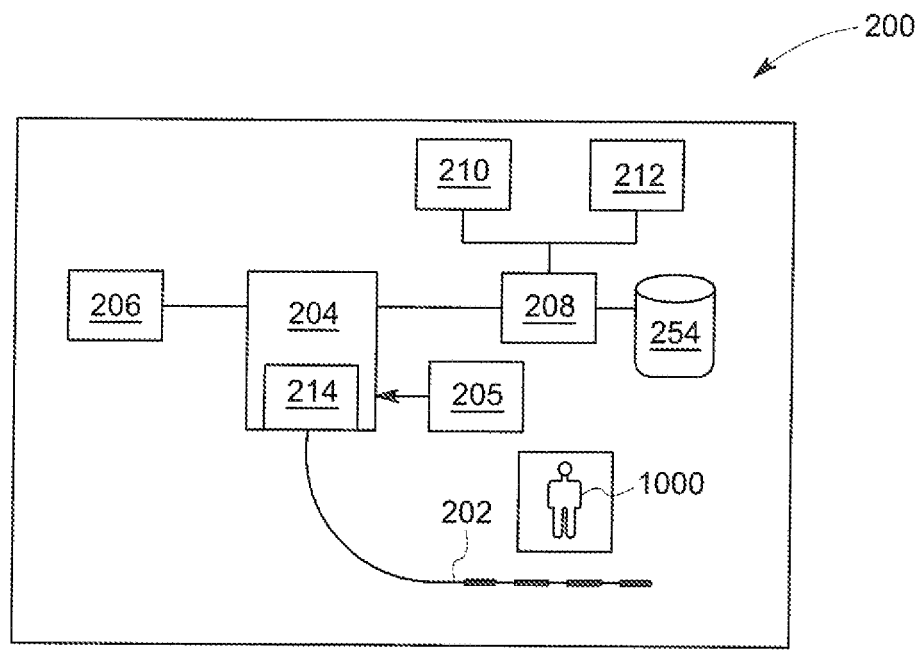
FIG. 1 is a schematic representation of an EP recording system including a catheter identification system according to one exemplary embodiment of the present invention.

FIG. 1 illustrates one exemplary embodiment of an electrophysiology (EP) mapping or an EP recorder system 200, such as those used in intracardiac electrocardiography (ECG) studies within the body of a patient 1000. These systems 200 receive an electrical signal (e.g., electrical current) via one or more catheters 202 from various locations of the body of the patient 1000, such as the heart. The system 200 can be similar to that disclosed in US Patent Application Publication No. US2013/0030482, which is expressly incorporated herein in its entirety. In the exemplary illustrated embodiment, the systems 200 includes an amplifier 204 that is operably connected between a signal generator 206 and a suitable computer, controller or central processing unit (CPU) 208. In operation, signals from the patient 1000, such as an ECG signal, is received by the amplifier 204 either via the catheter 202 or another catheter or device 205, and is processed by the amplifier 204 prior to transmitting the return signal to the CPU 208. The CPU 208 performs additional functions on the return signal and displays the information provided by the return signal on one or both of a real-time display 210 and a review display 212. The amplifier 204 also includes a catheter interface 214 that is used to connect the catheter 202 to the amplifier 204 for use with the recording or mapping system 200.

Figure 2:
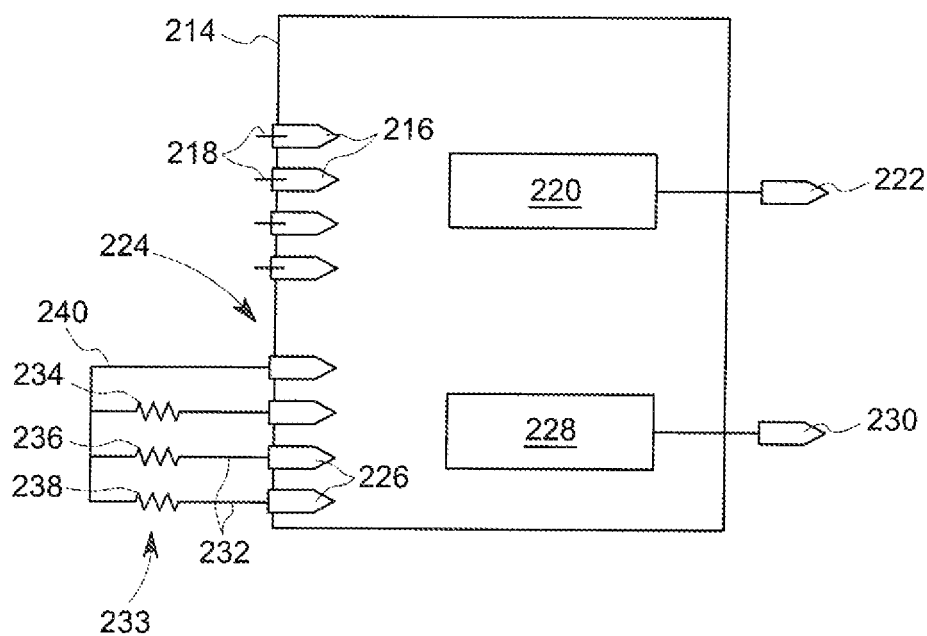
FIG. 2 is a schematic representation of the catheter identification interface for the recording system of FIG. 1 according to an exemplary embodiment of the invention.

In FIG. 2, one exemplary embodiment of a catheter interface 214 is illustrated. The interface 214 includes a number of pole sockets 216 that are configured to receive corresponding pins 218 disposed on the catheter 202 in order for the catheter 202 to be electrically coupled to the interface 214, and thus enable electric signals to pass between the interface 214 and the catheter 202. The pole sockets 216 are each connected to a catheter signal analog-to-digital converter (ADC) circuit 220 within the amplifier 204 in order to convert the analog signals form the pins 218 into digital signals that can be output from the ADC circuit 220 to the CPU 208 via the signal output 222 on the amplifier 204.

The interface 214 additionally includes a passive catheter identification system 224. The identification system 224 is formed in the illustrated exemplary embodiment with a number of catheter identification sockets 226 that are connected to an identification measurement ADC circuit 228, which in turn includes a signal output 230 connected to the CPU 208.

The sockets 226 are adapted to receive pins 232 located on the catheter 202 which are each connected to a resistor network 233 including identification resistors 234, 236, 238 and a return 240. The resistors 234-238 of the network 233 are operably connected to the catheter 202 in a suitable manner, such as directly to or within the cabling or cable connector (not shown) for the catheter 202 or in an adapter cable (not shown) engaged between the catheter 202 and the interface 214. Alternatively, the resistors 234-238 can be located within a custom catheter interface adaptor block (not shown) connected to the recorder or mapping system 200, such as those disclosed in US Patent Application Publication No. 2008/0255504, which is expressly incorporated herein by reference in its entirety.

Figure 4:
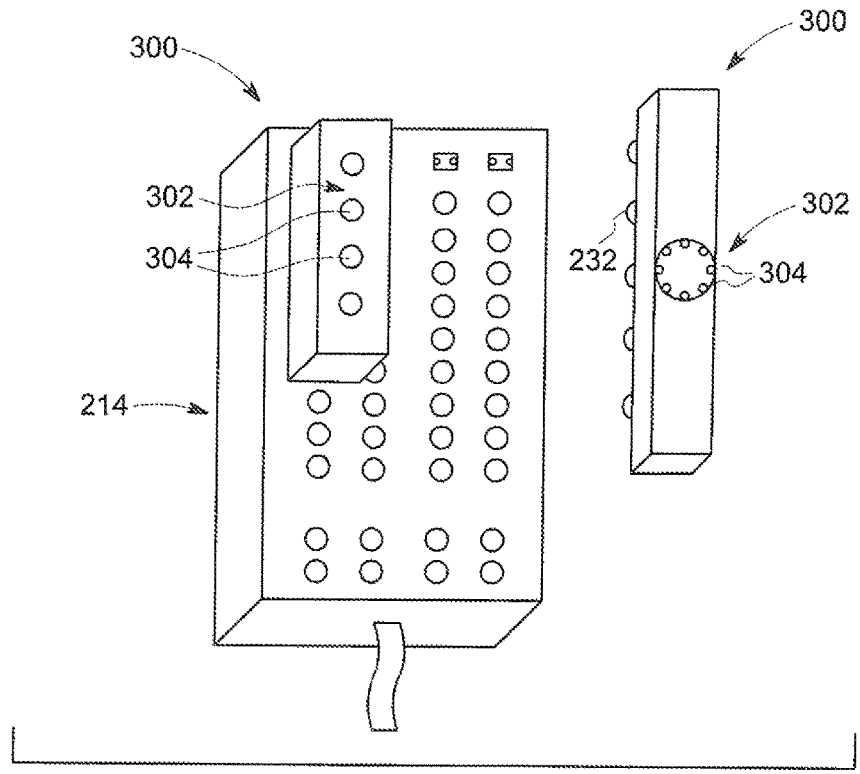
FIG. 4 is an isometric view of a catheter input module and catheter input plug according to one exemplary embodiment of the invention.

In still another embodiment, with reference to FIG. 4, the resistor network 233 can be disposed within an adapter block 300 configured to be positioned between the catheter 202 and the interface 214. The adapter 300 includes the pins 232 that are formed to be complementary to and engagable within the sockets 226 of the interface 214 on one end, and a catheter engagement structure 302 located opposite the pins 232. The catheter engagement structure 302 has a configuration of sockets 304 corresponding to the pin configuration for a particular type(s) of catheter 202 which may or may not be compatible with the arrangement of sockets 226 on the interface 214. Thus, a catheter 202 of virtually any type can be engaged with the adapter 300 to enable the catheter 202 to connect with the interface 214 having an otherwise incompatible socket configuration, while also providing the catheter 202 with the resistor network 233 corresponding to the catheter 202 for identification of the catheter 202 by the system 200 including the interface 214. The use of the adapter 300 enables a multi-pole catheter 202 connected to the block or adapter 300 to be engaged with the interface 214 on the amplifier 204 as one array, thus minimizing connection errors.

The resistors 234-238 are provided with particular resistance values that correspond to an attribute for the catheter 202 to which the resistors 234-238 are connected. For example, resistor 234 is provided with a resistance value that identifies the manufacturer of the catheter 202, resistor 236 is provided with a resistance value that identifies the type of catheter 202, and resistor 238 is provided with a resistance value that identified the number of poles present on the catheter 202. While the values provided to the individual resistors 234-238 can be selected in any suitable manner, the following tables illustrate some exemplary values for the resistors 234-238 to identify the manufacturer, type and number of poles on a given catheter 202:

TABLE 1

Resistor Values for Catheter Manufacturer ID

| MFG | ID Resistor Value in Ohms (Standard Value 1% tolerance) |
|---|---|
| MFG #1 | 1K |
| MFG #2 | 2.49K |
| MFG #3 | 4.99K |
| MFG #4 | 7.5K |
| MFG #5 | 10K |
| MFG #6 | 20K |
| MFG #7 | 40.2K |
| MFG #8 | 60.4K |
| MFG #9 | 80.6K |
| MFG #10 | 100K |

TABLE 2

Resistor Values For Catheter Type ID

| Type (Anatomical location) | ID Resistor value in Ohms (Standard Value 1% tolerance) |
|---|---|
| Ablation | 1K |
| Lasso | 2.49K |
| Steerable | 4.99K |
| Woven | 7.5K |
| HIS | 10K |
| HRA | 40.2K |
| CS | 80.6K |
| RVA | 100K |

TABLE 3

Resistor Values For Catheter Poles ID

| Number of Poles | ID Resistor value in Ohms (Standard Value 1% tolerance) |
|---|---|
| 2 | 1K |
| 4 | 2.0K |
| 6 | 3.01K |
| 8 | 4.02K |

TABLE 3-continued

Resistor Values For Catheter Poles ID

| Number of Poles | ID Resistor value in Ohms (Standard Value 1% tolerance) |
|---|---|
| 10 | 4.99K |
| 12 | 6.04K |
| 14 | 6.98K |
| 16 | 8.06K |
| 18 | 9.09K |
| 20 | 10K |
| 22 | 15K |
| 24 | 20K |
| 26 | 24.9K |
| 28 | 30.1K |
| 30 | 35.7K |
| 32 | 40.2K |
| 34 | 45.2K |
| 36 | 49.9K |
| 38 | 54.9K |
| 40 | 60.4K |
| 42 | 64.9K |
| 44 | 69.8K |
| 46 | 75K |
| 48 | 84.5K |
| 50 | 100K |

In each case, the value for a particular resistor 234-238 is selected to be sufficiently distinct and/or separated from the values of other resistors providing similar information about an attribute or property of a catheter 202 to avoid any confusion as to the information being provided by the particular resistor 234-238.

Figure 3:
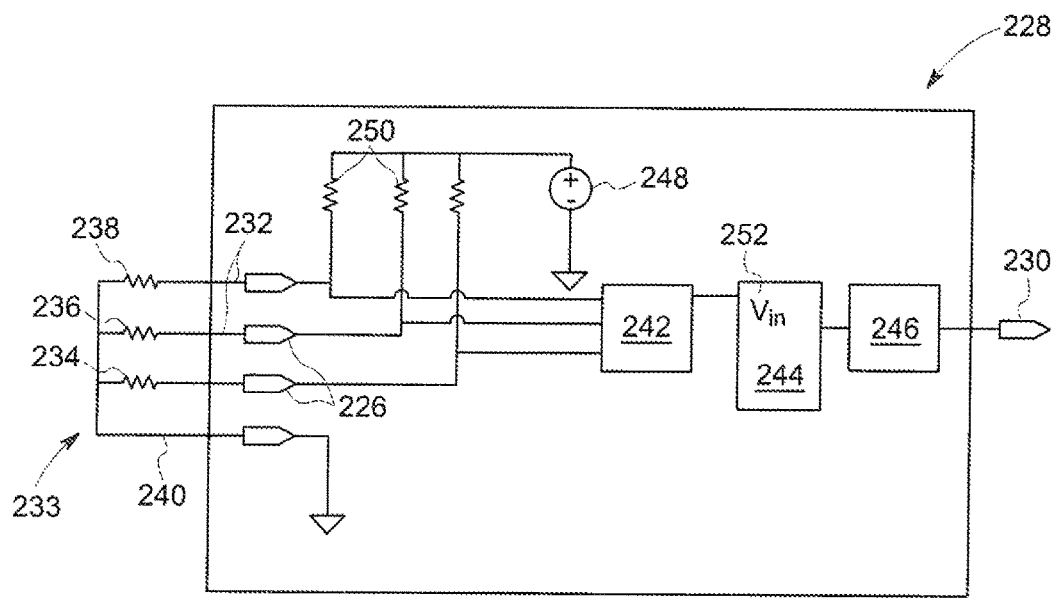
FIG. 3 is a schematic representation of identification resistor measurement circuit according to one exemplary embodiment the invention

Looking now at FIG. 3, an exemplary embodiment of the identification measurement ADC circuit 228 is illustrated. The circuit 228 is connected to the sockets 226 via a multiplexer 242 that operates to receive each of the signals from the sockets 226 and direct each one separately to an analog-to-digital converter (ADC) 244. The converter 244 is in turn connected to a digital interface circuit 246 that provides a digital signal regarding the values for each resistor 234-238 to the CPU 208 via the signal output 230.

The exemplary embodiment of the ADC circuit 228 also includes a reference voltage source 248. The reference voltage source 248, which is shown in the exemplary embodiment as a DC voltage source, is operably connected to each of the sockets 226. The connection between each socket 226 and the voltage source 248 includes a reference resistor 250 with a known value. With this construction, the identification system 224 operates in a passive manner by altering the signals sent through the identification resistors 234-238 that are utilized by the CPU 208 to determine the attributes of the catheter 202 including the resistors 234-238.

In operation, initially a catheter 202 is engaged with the identification measurement circuit 228 by the connection of the pins 232 on the catheter 202 with the sockets 226 in the interface 214. Once connected, the voltage source 248 sends an identification signal having a known voltage across the reference resistors 250 and to each of the identification resistors 234-238. The voltage of the identification signals across each identification resistor 234-238 is altered corresponding to the resistance of the reference resistors 250 and the individual identification resistor 234, 236 or 238. These altered identification signals are subsequently directed into the multiplexer 242 which individually transmits the altered identification signal associated with each identification resistor 234-238 to the input 252 of the ADC 244. The individual digitized altered identification signals are output from the ADC 244 to the interface circuit 246 and subsequently to the CPU 208. Upon reaching the CPU 208, the CPU 208 can utilize the altered identification signal in conjunction with a reference database 254 operably connected to the CPU 208 and in which the look up tables containing the information on the identification resistor values is stored. In comparing the altered identification signals output from the circuit 228 with the tables in the database 254, the CPU 208 can determine the various attributes represented by the altered identification signals from the identification resistors 234-238. With the ability to quickly and clearly identify catheters 202 utilizing the system 224, the potential is that the use of the system 224 comes to be employed as an overall industry standard for catheter configuration due to the simplistic nomenclature implicit to the resistor identification scheme used with the system 224.

In another exemplary embodiment of the invention, the resistor network 233 and identification circuit 228 of the identification system 224 provide the system 224 with the capability to monitor the connection resistance through the identification circuit 228. By utilizing the altered identification signals output from the circuit 228 to the CPU 208, and knowing the values for the reference resistors 250 and identification resistors 234-238, the CPU 208 can determine the variance of the expected altered identification signal value output from the circuit 228 with the actual altered identification signal value. In doing so, the passive identification system 224 provides the recording or mapping system 200 with a reference value or spec to compare with the variance to the standard specifications for the catheter 202/interface 214 connection, which can alert the system 200 to potential connectivity issues. In this manner, the identification system 224 and/or circuit 228 can function as a measurement quality calibration/quality check on the connection between the catheter 202 and interface 214 to highlight poor resistance connections which typically increase noise susceptibility of the system 200 and can be a sign of worn signal path cabling, or other issues with the catheter 202.

The identification system 224 also enables automated device configuration by the system 200 such that the system 200 knows what type of catheter 202 is connected, and where that catheter 200 is connected with respect to the interface 214. This system and method of catheter identification and configuration leads to the ability to record the use of the particular catheter 202 with the system 200, in order to more accurately define the useful life for the catheter 202. In addition, the identification system 224 enables the system 200 to define study configurations based on the actual catheter(s) 202 connected to the system 200 rather than current methods, i.e. the catheter configuration could be set based on the catheter 202 being used during the procedure. In addition, while the system 202 can be physically set up and/or defined by the physician when connecting the catheter(s) 202 to the system 200, suitable computer software in the system 200 can also be employed to respond directly to the types of catheter(s) 202 connected to the system 200, such as by automatically loading a configuration for the catheter(s) 202 from memory, i.e., database 254, to speed-up procedure set-up time.

In alternative embodiments for the system 224, the number of resistors 234-238 utilized can be varied to provide less or additional information about the particular catheter 202. In one exemplary embodiment, eight (8) separate identification resistors 234 can be used in the resistor network 233. Further, in addition to the resistor network 233, a color code indicator (not shown) can be displayed on the exterior of the catheter 202 to provide visual identification to the type of catheter 202 in addition to the information provided by the identification system 224 integrated within the catheter 202, such as, for example white for a quad pole catheter 202, blue for a decca pole catheter 202, etc. This color can be transferred to the display 203 such that the color coding on the exterior of the catheter 202 matches the color configuration of the signals drawn on the display 203 for the recording system 200, thus providing the user with an end-to-end visual confirmation of correct configuration of the catheter 202.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A catheter identification system for providing information about one or more attributes of a catheter connectable to an electrophysiology (EP) recording or mapping system, the identification system comprising:
   a) a catheter;
   b) a resistor network operably connected to the catheter, the resistor network including at least one identification resistor and a return connected to the at least one identification resistor; and
   c) an identification resistor measurement circuit operably connected to the catheter and configured to send an identification signal through the at least one resistor in the resistor network to retrieve an altered identification signal from the identification resistor, where the altered identification signal provides information on an attribute of the catheter.

2. The identification system of claim 1 wherein the resistor network is positioned within the catheter.

3. The identification system of claim 1 wherein the resistor network is positioned within an adapter configured to connect the catheter to the identification resistor measurement circuit.

4. The identification system of claim 3 wherein the adapter is operably connected between the at least one resistor and a catheter interface operably connected to the identification resistor measurement circuit to minimize connection errors between the resistor network and the identification resistor measurement circuit.

5. The identification system of claim 1 further comprising a database operably connected to the identification resistor measurement circuit, the database including a table of attributes for the catheter corresponding to the altered identification signal.

6. The identification system of claim 1 wherein the resistor network includes multiple identification resistors, each identification resistor providing an individual altered identification signal representative of a different attribute of the catheter.

7. The identification system of claim 1 wherein the identification system operates in a passive manner.

8. The identification system of claim 1 wherein the identification resistor measurement circuit includes a voltage source for supplying the identification signal to the resistor network.

9. The identification system of claim 8 further comprising:
   a) a number of pins on the catheter, each pin operably connected to an identification resistor in the resistor network; and
   b) a number of sockets operably connected to the voltage source and engageble with the pins.

10. The identification system of claim 8 wherein the identification resistor measurement circuit is located within a catheter interface operably connected to the EP system.

11. The identification system of claim 10 wherein the identification resistor measurement circuit is operably connected to a CPU for the EP system.

12. The identification system of claim 11 wherein the CPU is configured to define an operational study configuration for the EP system using the information on the attributes of the catheter from the altered identification signal.

13. An EP system for obtaining and recording information on a patient connected to the EP system, the EP system comprising:
   a) an amplifier including a catheter interface;
   b) a computer operably connected to the amplifier;
   c) at least one catheter connected to the catheter interface; and
   d) a passive catheter identification system operably connected between the at least one catheter and the catheter interface, the identification system comprising:
      a. an identification resistor measurement circuit engaged with the catheter interface and operable to output an identification signal; and
      b. an identification resistor network engaged with the at least one catheter and operably engageble with the identification resistor measurement circuit, the resistor network including at least two identification resistors each capable of receiving the identification signal and outputting an altered identification signal indicative of different attributes of the catheter, and a return connected to the at least two identification resistors.

14. The EP system of claim 13 wherein the computer is configured to define an operational study configuration for the EP system using the information on the attributes of the catheter from the altered identification signal.

* * * * *